US011399753B2

(12) United States Patent
Achmann et al.

(10) Patent No.: US 11,399,753 B2
(45) Date of Patent: Aug. 2, 2022

(54) ELECTROCHEMICAL SENSOR AND METHOD FOR PRODUCING THEREOF

(71) Applicant: Roche Diabetes Care, Inc., Indianapolis, IN (US)

(72) Inventors: Sabine Achmann, Mannheim (DE); Stephan-Michael Frey, Pfungstadt (DE); Sebastian Pankalla, Ludwigshafen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/854,615

(22) Filed: Apr. 21, 2020

(65) Prior Publication Data
US 2020/0245908 A1    Aug. 6, 2020

Related U.S. Application Data

(63) Continuation of application No. PCT/EP2018/078960, filed on Oct. 23, 2018.

(30) Foreign Application Priority Data

Oct. 24, 2017    (EP) .................................... 17198040

(51) Int. Cl.
*A61B 5/1468* (2006.01)
*A61B 5/1486* (2006.01)
*A61B 5/145* (2006.01)

(52) U.S. Cl.
CPC .......... *A61B 5/1486* (2013.01); *A61B 5/1468* (2013.01); *A61B 5/14532* (2013.01); *A61B 2562/16* (2013.01)

(58) Field of Classification Search
CPC ... A61B 5/1468; A61B 5/1473; A61B 5/1486; A61B 5/14865; A61B 5/14532;
(Continued)

(56) References Cited

U.S. PATENT DOCUMENTS 6,134,461 A     10/2000  Say et al.
2004/0133164 A1  7/2004  Funderburk et al.
(Continued)

FOREIGN PATENT DOCUMENTS

CN    102387746 A    3/2012
CN    103519827 A    1/2014
(Continued)

OTHER PUBLICATIONS

International Search Report and Written Opinion of the International Searching Authority, PCT/EP2018/078960, dated Jan. 23, 2019, 10 pages.

*Primary Examiner* — Christian Jang
(74) *Attorney, Agent, or Firm* — Bose McKinney & Evans LLP

(57) ABSTRACT

An electrochemical sensor is disclosed. The sensor has a substrate having a proximal part and an elongated distal part. Electrodes are formed on the distal part. The working electrode forms a conductive trace and multiple electrode pads are arranged along and connected by conductive trace. The electrode pads include a corrosive conductive layer covered by a non-corrosive conductive layer. The corrosive conductive layer is a metal less noble or as noble as Ag, and the non-corrosive conductive is a metal more noble than Ag. An insulating layer on the substrate has openings in the areas of the electrode pads. A protective measure for the corrosive conductive layer can be provided, such as having the insulating layer at least partially overlap the electrode pad edges, or providing at least one of the electrode pads with an elongated shape along the smaller dimension of the distal part.

18 Claims, 7 Drawing Sheets

(58) Field of Classification Search
CPC ............ A61B 5/14535; A61B 5/14539; A61B 5/14546; A61B 2562/125; A61B 2562/16; G01N 27/327; G01N 27/3271; G01N 27/3273
See application file for complete search history.

(56) References Cited

U.S. PATENT DOCUMENTS

| | | |
|---|---|---|
| 2007/0240986 A1 | 10/2007 | Reymond et al. |
| 2008/0021436 A1 | 1/2008 | Wolpert et al. |
| 2010/0200538 A1 | 8/2010 | Petisce et al. |
| 2010/0230285 A1 | 9/2010 | Hoss et al. |
| 2011/0028815 A1 | 2/2011 | Simpson et al. |
| 2011/0028816 A1* | 2/2011 | Simpson ............ A61B 5/14517 600/345 |
| 2012/0016220 A1 | 1/2012 | Hauer et al. |
| 2014/0005492 A1 | 1/2014 | Harttig |
| 2015/0099954 A1* | 4/2015 | Achmann ............ A61B 5/1473 600/345 |
| 2015/0316501 A1* | 11/2015 | Wu ...................... A61B 5/1486 204/401 |
| 2016/0235346 A1* | 8/2016 | Liu ...................... A61B 5/6849 |

FOREIGN PATENT DOCUMENTS

| | | |
|---|---|---|
| EP | 2 348 964 B1 | 5/2013 |
| WO | WO 2014/001382 A1 | 1/2014 |

* cited by examiner

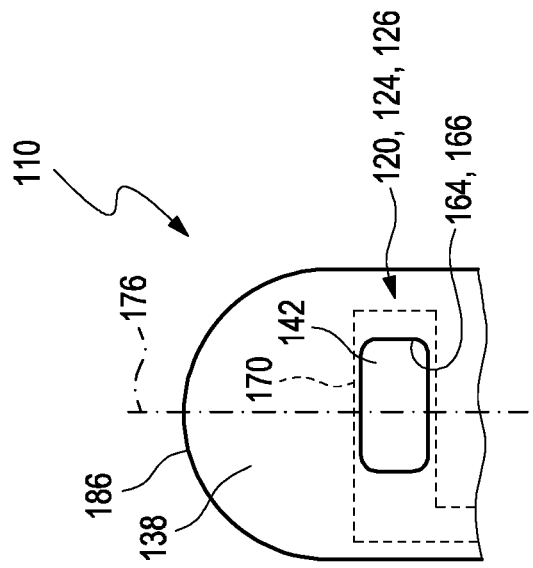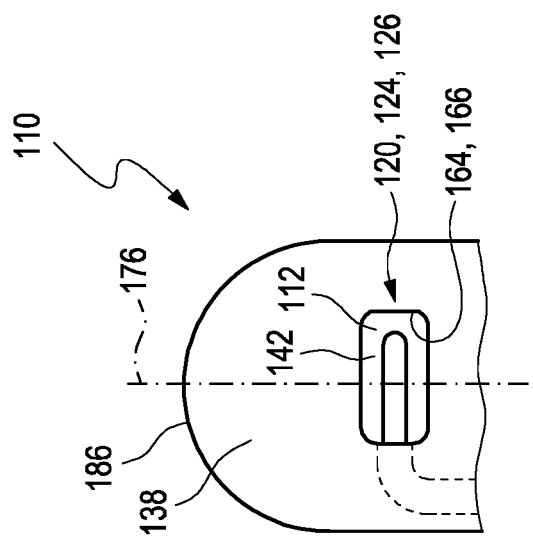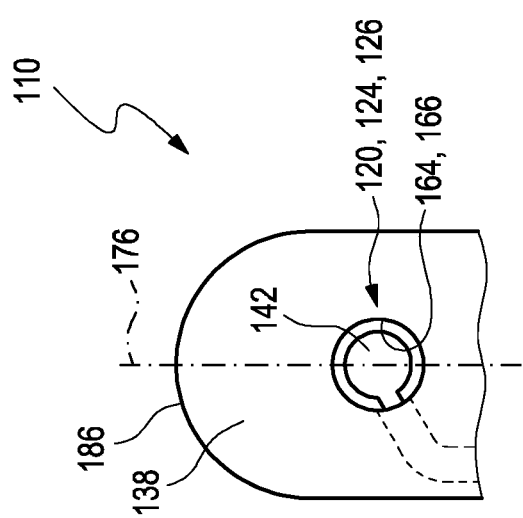

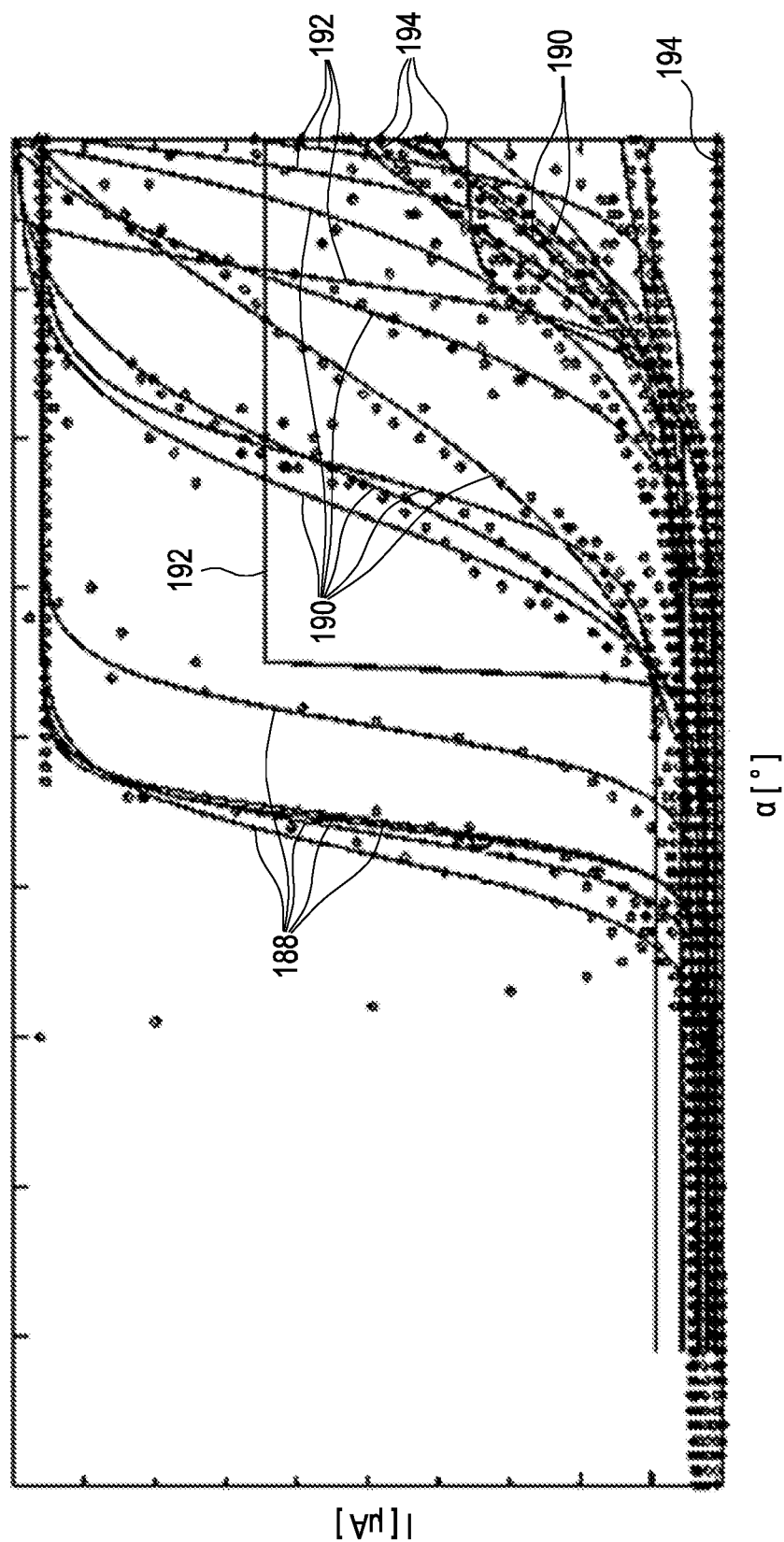

ELECTROCHEMICAL SENSOR AND METHOD FOR PRODUCING THEREOF

RELATED APPLICATIONS

This application is a continuation of PCT/EP2018/078960, filed Oct. 23, 2018, which claims priority to EP 17 198 040.2, filed Oct. 24, 2017, both of which are hereby incorporated herein by reference.

BACKGROUND

The present disclosure relates to an electrochemical sensor and a method for producing the electrochemical sensor. The electrochemical sensor specifically may be adapted for detecting at least one analyte in a body fluid. More specifically, the electrochemical sensor may be an electrochemical sensor configured for insertion into a body tissue of the user, specifically an insertable or implantable electrochemical sensor for long-term monitoring of the at least one analyte in the body tissue and/or in a body fluid within the body tissue. The electrochemical sensor may both be applied in the field of home care and in the field of professional care, such as in hospitals. Other applications are feasible.

Monitoring certain body functions, more particularly monitoring one or more concentrations of at least one metabolite concentration in a body fluid plays an important role in the prevention and treatment of various diseases. Such metabolites can include by way of example, but not exclusively, blood glucose, lactate, cholesterol or other types of analytes and metabolites. Without restricting further possible applications, embodiments will be described in the following text with reference to blood-glucose monitoring. However, additionally or alternatively, this disclosure can also be applied to other types of analytes, such as the analytes mentioned above.

In the field of continuous or long-term monitoring, the setup and the manufacturing of the sensors is a technical challenge. Typically, electrochemical sensors are used which transcutaneously are inserted into the body tissue of the user. The sensors typically comprise an elongated flexible substrate onto which a plurality of electrodes, including one or more working electrodes and one or more further electrodes such as one or more counter electrodes and/or one or more reference electrodes are applied.

U.S. Publication No. 2010/0200538 A1 discloses methods for fabricating analyte sensor components, using IC- or MEMs-based fabrication techniques and sensors prepared therefrom. Fabrication of the analyte sensor component comprises providing an inorganic substrate having deposited thereon a release layer, a first flexible dielectric layer and a second flexible dielectric layer insulating there between electrodes, contact pads and traces connecting the electrodes and the contact pads of a plurality of sensors. Openings are provided in one of the dielectric layers over one or more of the electrodes to receive an analyte sensing membrane for the detection of an analyte of interest and for electrical connection with external electronics. The plurality of fabricated sensor components are lifted off the inorganic substrate.

EP 2348964 B1 discloses an electrode system for measuring the concentration of an analyte under in-vivo conditions. The electrode system comprises a counter-electrode having an electrical conductor, a working electrode having an electrical conductor on which an enzyme layer containing immobilized enzyme molecules for catalytic conversion of the analyte is arranged, and a diffusion barrier that slows the diffusion of the analyte from body fluid surrounding the electrode system to enzyme molecules down. The invention provides the enzyme layer in the form of multiple fields that are arranged on the conductor of the working electrode at a distance from each other.

WO 2014/001382 A1 describes a sensor element for determining the concentration of at least one analyte in a body fluid. The sensor element is at least partially implantable into a body tissue. The sensor element has a substrate and at least two electrodes, the electrodes comprising at least one working electrode and at least one counter electrode. The working electrode comprises at least one conductive pad applied to the substrate, wherein at least one electrically conductive sensor material is applied to the conductive pad. The electrically conductive sensor material comprises at least one detector substance adapted to perform an electrically detectable electrochemical detection reaction with the analyte. The counter electrode comprises at least one counter electrode conductive pad applied to the substrate. The sensor element further comprises at least one electrically insulating material. The electrically insulating material surrounds the counter electrode on all sides. A height of the electrically insulating material at least equals the height of the counter electrode conductive pad.

Despite the advantages of these known sensors for transcutaneous insertion, a large number of technical challenges remain. Thus, specifically, one technical challenge arises from the fact that many electrochemical sensors configured for long-term monitoring of one or more analytes in a body tissue are typically subject to mechanical stress. Once inserted into the body tissue, the electrochemical sensors typically are stressed by mechanical bending, pulling and pushing forces. Further influences are based on chemical effects, such as oxidation. Due to this mechanical and chemical stress, a technical challenge specifically resides in avoiding a delamination of the metal electrodes from the substrate of the sensor.

SUMMARY

This disclosure teaches an electrochemical sensor, specifically for insertion and/or implantation into a body tissue, more specifically an electrochemical sensor for long-term monitoring of at least one analyte in a body fluid, which at least partially addresses the above-mentioned technical challenges. Specifically, an electrochemical sensor is taught which provides an improved long-term stability, more specifically under real conditions such as mechanical and chemical stress as typically applied in an inserted state.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "electrode," "conductive pad," "trace," and "conductive layer," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, an electrochemical sensor is disclosed, specifically for detecting an analyte in a body fluid, more specifically an electrochemical sensor for insertion of a body tissue of the user. The electrochemical sensor comprises a substrate having a proximal part and an elongated distal part. At least one working electrode, at least one reference electrode and at least one counter electrode are formed on the distal part. The working electrode comprises a conductive trace along which multiple electrode pads are arranged that are connected via the conductive trace. The electrode pads include a corrosive conductive layer covered by a non-corrosive conductive layer. An insulating layer is disposed on the substrate leaving openings in the area of the electrode pads.

For addressing the above-mentioned technical challenges, the electrochemical sensor comprises at least one protective measure for the corrosive conductive layer selected from the group consisting of:

a. the insulating layer at least partially overlaps on at least one electrode pad edge of at least one of the electrode pads;

b. at least one of the electrode pads has an elongated shape along the smaller dimension of the elongated distal part.

The term "sensor" as used herein is a broad term and is to be given its ordinary and customary meaning to a person of ordinary skill in the art and is not to be limited to a special or customized meaning. The term specifically may refer, without limitation, to an arbitrary element or device configured for detecting at least one condition or for measuring at least one measurement variable. The sensor specifically may be or may comprise an analyte sensor for at least partial implantation into a body tissue of a user, more specifically an analyte sensor for continuous monitoring of the analyte. The sensor specifically may be a monolithic sensor element.

Consequently, the term "electrochemical sensor" specifically may refer to a sensor as defined above which is based on electrochemical measurement principles, such as by using one or more of an amperometric or a potentiometric measurement principle. Specifically, as will be outlined in further detail above, the electrochemical sensor may comprise at least one enzyme configured for performing at least one redox reaction in the presence of the analyte to be detected, wherein the redox reaction may be detected by electrical means.

Further, the term "analyte" as used herein is a broad term and is to be given its ordinary and customary meaning to a person of ordinary skill in the art and is not to be limited to a special or customized meaning. The term specifically may refer, without limitation, to an arbitrary element, component or compound which may be present in a body fluid and the concentration of which may be of interest for a user. Specifically, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined.

The term "user" as used herein is a broad term and is to be given its ordinary and customary meaning to a person of ordinary skill in the art and is not to be limited to a special or customized meaning. The term specifically may refer, without limitation, to a human being or an animal, independent from the fact that the human being or animal, respectively, may be in a healthy condition or may suffer from one or more diseases. As an example, the user may be a human being or an animal suffering from diabetes. However, additionally or alternatively, this disclosure may be applied to other types of users.

Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The sensor may fully or partially be implanted into the body tissue, specifically transcutaneously. The sensor specifically may have a length of no more than 50 mm, e.g., a length of 2 mm to 30 mm. The sensor further may have a width of no more than 5 mm, e.g., a width of 0.5 mm to 2 mm. The sensor specifically may be a flexible sensor being deformable under typical forces occurring in an implanted state. The sensor may have a thickness of no more than 2 mm, preferably a thickness of 0.2 to 1.0 mm. The sensor specifically may be strip-shaped, having the shape of a thin elongated strip. The sensor specifically may be biocompatible, e.g., by having a biocompatible coating.

The term "substrate" as used herein is a broad term and is to be given its ordinary and customary meaning to a person of ordinary skill in the art and is not to be limited to a special or customized meaning. The term specifically may refer, without limitation, to an element which carries one or more further elements of a device. The substrate, specifically, may be a flat substrate, such as a substrate comprising one or more files or layers. The substrate specifically may be flexible and/or deformable. Thus, as an example, the substrate may be a thin, flexible substrate, such as a substrate made of polyimide. As an example, the substrate may have a thickness of 50 μm to 1 mm, specifically a thickness of 100 μm to 500 μm, such as 200 to 400 μm.

The term "proximal" as used herein is a broad term and is to be given its ordinary and customary meaning to a person of ordinary skill in the art and is not to be limited to a special or customized meaning. The term specifically may refer, without limitation, to a direction or side which is closer to a user when holding or contacting an element. Consequently, the term "distal" as used herein specifically may refer to an opposite direction or side, which is further away from the user when holding or contacting the element. In the context of the electrochemical sensor, the proximal part specifically may form the part which is contacted by an electronics unit, such as a transmitter, whereas the distal part may fully or partially be implanted or inserted into the body tissue. Similarly, as will be used in further detail below, the term "distal end" specifically may refer to end of the substrate and/or an end of the electrochemical sensor which the farthest protrudes into the body tissue.

The term "elongated" as used herein is a broad term and is to be given its ordinary and customary meaning to a person of ordinary skill in the art and is not to be limited to a special or customized meaning. The term specifically may refer, without limitation, to an element having a length and a width, wherein the length exceeds the width, e.g., by at least a factor of 1.5, at least a factor of 2.0, at least a factor of 5.0, at least a factor of 10 or even a factor of 15 or more. In the context of the distal part of the substrate, the elongated shape specifically may refer to the fact that the distal part extends along a longitudinal axis, e.g., having the shape of a strip with a length l parallel to the longitudinal axis and a width w perpendicular to the longitudinal axis.

The terms "working electrode," "reference electrode" and "counter electrode" as used herein are broad terms and are to be given their ordinary and customary meaning to a person of ordinary skill in the art and are not to be limited to a special or customized meaning. The term "working electrode" specifically may refer, without limitation, to an electrode of the electrochemical sensor which is configured for measuring a signal, such as a voltage or electrical potential, dependent on the degree of an electrochemical detection reaction taking place at the working electrode, for the purpose of detecting the at least one analyte. As will be outlined in further detail below, the working electrode specifically may comprise at least one enzyme. The term "reference electrode" specifically may refer, without limitation, to an electrode of the electrochemical sensor which is configured to provide an electrochemical reference potential which, at least widely, is independent of the presence or absence or concentration of the analyte. The reference electrode specifically may comprise Ag/AgCl. The term "counter electrode" specifically, without limitation, may refer to an electrode of the electrochemical sensor which is configured to balance an electrical current through the working electrode, e.g., in order to avoid large electrical currents through the reference electrode. The counter electrode specifically may comprise Ag/AgCl. For exemplary embodiments, as an example, reference may also be made to the above-mentioned prior art, e.g., to EP 2348964 B1.

The term "conductive trace" as used herein is a broad term and is to be given its ordinary and customary meaning to a person of ordinary skill in the art and is not to be limited to a special or customized meaning. The term specifically may refer, without limitation, to an electrically conductive strip, layer, wire or other type of elongated electrical conductor which extends at least partially along the elongated distal part and which may be configured to electrically connect the working electrode with at least one working electrode contact pad. Thus, the conductive trace may be configured to electrically interconnect the multiple electrode pads and, further, to connect the multiple electrode pads of the working electrode with at least one working electrode contact pad, which, as an example, may be located within the proximal part of the substrate.

The term "electrode pad" as used herein is a broad term and is to be given its ordinary and customary meaning to a person of ordinary skill in the art and is not to be limited to a special or customized meaning. The term specifically may refer, without limitation, to a flat electrically conductive element disposed on a substrate. As an example and as will be outlined in further detail below, the electrode pads may comprise two or more electrically conductive layers directly or indirectly disposed on the substrate, the electrically conductive layers having a limited lateral extension, thereby forming an electrically conductive area on the substrate. As an example, the electrically conductive area may have the shape of a rectangle, a polygon, a circle, an oval or a strip.

The term "corrosive conductive layer" as used herein is a broad term. The term may refer to a corroding conductive layer. The corroding conductive layer may be decomposable by a corrosive agent. The term specifically may refer, without limitation, to an electrically conductive layer which comprises at least one corrosive material being prone to decomposition or reaction, such as by oxidation or by reaction with a corrosive agent, such as water and/or oxygen. The corrosive material, specifically, may comprise at least one material which, specifically under the electrochemical conditions used in the electrochemical sensor, is oxidized. As an example, the corrosive material may be a material which is oxidized when applying a voltage of 350 mV between an electrode made of the corrosive material and an electrode made of Ag/AgCl.

Similarly, the term "non-corrosive conductive layer" may refer, without limitation, to an electrically conductive layer which comprises at least one non-corrosive material, i.e., a material which is not corrosive in the above-mentioned sense. Thus, the term "non-corrosive conductive layer" may refer to a non-corroding conductive layer. The non-corroding conductive layer may be resistant against decomposition or reaction, such against oxidation or reaction with a corrosive agent, such as water and/or oxygen, at least to a large extent. Exemplary embodiments will be given in further detail below. As an example, the corrosive conductive layer and the non-corrosive conductive layer each may have a thickness of 100 nm to 2 μm.

Specifically, the corrosive conductive layer may be in direct contact with the substrate. The non-corrosive conductive layer may be in direct contact with the corrosive conductive layer. Thus, the corrosive conductive layer may function as an adhesive layer which helps to improve adhesion of the non-corrosive conductive layer to the substrate or the electrochemical sensor. The corrosive conductive layer may be bound to the substrate by a material bond connection, and, similarly, the non-corrosive conductive layer may be bound to the corrosive conductive layer by a material bond connection.

The non-corrosive conductive layer specifically may fully cover the corrosive conductive layers such that no part of a region of the corrosive conductive layer is, at least when no mechanical load is exerted onto the electrochemical sensor, exposed to ambient air. Specifically, the non-corrosive conductive layer may overlap the corrosive conductive layer at the edges, such that a partial pad formed by the non-corrosive conductive layer is slightly larger than a partial pad underneath formed by the corrosive conductive layer. Alternatively, however, the non-corrosive conductive layer and the corrosive conductive layer may also have identical dimensions with respect to their lateral extensions.

The term "insulating layer" as used herein is a broad term and is to be given its ordinary and customary meaning to a person of ordinary skill in the art and is not to be limited to a special or customized meaning. The term specifically may refer, without limitation, to a layer made of at least one electrically insulating material. Specifically, the at least one electrically insulating material may comprise at least one electrically insulating organic material, such as at least one resin or resist, e.g., a solder resist. The thickness of the insulating material specifically may exceed the thickness of the electrode pads and, further, may also exceed the overall thickness of the working electrode, including optionally the at least one test chemical.

The openings may fully or partially be surrounded by the at least one insulating layer. Thus, as will be outlined in further detail below, the openings specifically may form windows through which the working electrode at least partially is accessible for the at least one analyte to be detected. The rim of the openings may fully or partially be formed by the at least one insulating layer.

The term "protective measure" as used herein is a broad term and is to be given its ordinary and customary meaning to a person of ordinary skill in the art and is not to be limited to a special or customized meaning. The term specifically may refer, without limitation, to an arbitrary device or setup which is suited to protect the at least one corrosive conductive layer, e.g., mechanically and/or electrochemically. Thus, specifically, the protective measure may comprise at least one device or layer setup which is suited to reduce mechanical stress onto the at least one corrosive conductive layer, as compared to a situation in which the protective measure is not present. Additionally or alternatively, the protective measure may comprise at least one device or layer setup which is suited to prevent aggressive substances from entering reaching the corrosive conductive layer. The general idea, specifically, may reside in the finding that the above-mentioned technical challenges of providing an improved stability against delamination and stress may be addressed by providing protective measures which protect the corrosive conductive layer, e.g., from external influences such as electrochemical oxidation and/or from mechanical stress.

The first option for the at least one protective measure, as outlined above, includes overlapping the at least one edge with the at least one electrically insulating layer. Thus, when looking onto the substrate from the top, the edge may, at least partially, be covered by the insulating layer and, thus, may, at least partially, not be visible from the top. Thereby, the edge may be protected both mechanically and chemically. Thus, as an example, by the overlapping insulating layer, the edge may be protected against mechanical lift-off and/or may be protected against ingression of oxidizing liquids. The insulating layer may overlap the edge, as an example, by at least 5 μm, such as by 5 μm to 200 μm, e.g., 20 μm to 100 μm. The insulating layer may overlap the at least one electrode pad edge circumferentially on the full edge of the electrode pad. Thus, as an example, the full circumferential edge of the electrode pad may be overlapped by the insulating layer, without leaving parts of the edge non-overlapped.

The second option for the at least one protective measure, which may be implemented additionally or alternatively to the first option, may include providing at least one of the electrode pads, preferably all of the electrode pads, having an elongated shape in a direction parallel to a smaller dimension of the elevated distal part. Thus, as an example, the elevated distal part may extend along a longitudinal axis, and the at least one electrode pad may be elongated with a longer axis perpendicular to the longitudinal axis. As will be shown in detail below, measurements and simulations of mechanical stress during use of the electrochemical sensor show that the elongated substrate, in use, typically is bent about a bending axis perpendicular to the longitudinal axis, whereas bending about an axis parallel to the longitudinal axis takes place at a lesser extent. Bending about the axis perpendicular to the longitudinal axis, however, induces a mechanical stress onto the electrode pads specifically in case the electrode pads extend over a large distance in the longitudinal direction. Consequently, the extent of the electrode pads in the longitudinal direction may be reduced as compared to the extension in a direction perpendicular to the longitudinal direction, thereby creating the elongate shape along the smaller dimension of the elongated distal part.

The electrochemical sensor may be further embodied in various ways. Thus, specific embodiments may refer to the corrosive conductive layer and the non-corrosive conductive layer. As outlined above, the at least one corrosive conductive layer specifically may be interposed in between the non-corrosive conductive layer and the substrate. The non-corrosive conductive layer specifically may comprise at least one material more noble than silver (Ag), specifically at least one metal nobler than Ag. The at least one non-corrosive conductive layer specifically may comprise at least one material having a standard potential of more than +0.8 V. The corrosive conductive layer specifically may comprise at least one material at most as noble as Ag, specifically at least one metal being less noble or, at most, as noble as Ag. The corrosive conductive layer specifically may comprise at least one material having a standard potential of no more than +0.8 V.

The non-corrosive conductive layer specifically may comprise at least one material selected from the group consisting of: palladium (Pd); gold (Au); platinum (Pt); carbon; graphite; an organic conductor, specifically a conductive polymer; an organic semiconductor, specifically a semiconducting polymer, such as Poly-3,4-ethylendioxythiophen (PEDOT) or PEDOT:PSS. For the examples given in further detail below, Au will be used, without restricting further embodiments. This is mainly due to the fact that Au may easily be applied, e.g., by using wet-chemical processes such as chemical metallization or galvanic deposition, and, further, since Au provides excellent surface qualities for the electrode pads. It shall be noted, however, that other deposition techniques and/or other metals, conductive materials or combinations of conductive materials are possible for the non-corrosive conductive layer.

The corrosive conductive layer specifically may comprise at least one material selected from the group consisting of: copper (Cu); titanium (Ti); aluminum (Al); silver (Ag). For the examples given in further detail below, Cu will be used, without restricting further embodiments. This is mainly due to the fact that Cu provides excellent adhesive properties to many substrates, such as polyimide substrates, and, further, provides an excellent surface for the position of further metals or other conductive materials, e.g., by using wet-chemical processes such as chemical metallization or galvanic deposition. Cu itself may be applied e.g., wet-chemically to the substrate, e.g., from a solution in a deposition bath. It shall be noted, however, that other deposition techniques and/or other metals, conductive materials or combinations of conductive materials are possible for the corrosive conductive layer.

Specifically, the electrode pad, one of the electrode pads, more of the electrode pads or even all of the electrode pads of the at least one working electrode may comprise at least one corrosive conductive layer—non-corrosive conductive layer pair selected from the group consisting of: Cu—Au; Cu—Pd; Cu—Pt. As outlined above, in the following, without restricting further embodiments, the combination Cu—Au will be used.

As outlined above, the at least one working electrode may comprise at least one test chemical. Thus, as an example, the electrode pads of the working electrode may fully or partially be covered with at least one test chemical, specifically at least one test chemical comprising at least one enzyme for detecting the at least one analyte. Examples for enzymes which may be used also in the context of this disclosure may be derived from the prior art documents listed above. As an example, glucose oxidase (GOx) and/or glucose dehydrogenase (GOD) may be used. The test chemical, further, may comprise additional materials, such as binder materials, electrode particles, mediators or the like. Thus, as an example, the test chemical may comprise at least one enzyme, carbon particles, a polymer binder and $MnO_2$-particles. Further, the at least one test chemical may be comprised in a single layer, or the test chemical may comprise a plurality of layers, such as one layer having the at least one enzyme and one or more additional layers having one or more additional functions, such as one or more diffusion barriers and/or one or more biocompatibility layers.

As an example, the insulating layer may form openings on the electrode pads, such as windows. The openings may fully or partially be filled with the at least one test chemical. As outlined above, the openings may be dimensioned such that the edge of the electrode pad is fully or partially overlapped by the insulating layer. Consequently, the openings may be dimensioned smaller than the electrode pads underneath, such that, when looking through the openings onto the electrode pads underneath, the edges of the electrode pads preferably are not visible. These openings then may fully or partially be filled with the at least one test chemical, e.g., with one bottom layer comprising the enzyme, the bottom layer contacting the noncorrosive conductive layer, and, optionally, with one or more layers on top of the bottom layer, such as one or more diffusion barriers and/or one or more biocompatibility layers, also referred to as biocompatible coating.

As outlined above, in the second option of the protective measure, the electrode pads may have an elongated shape in a direction perpendicular to a longitudinal axis of extension of the substrate. The electrode pads specifically may have an elongated shape having a maximum width w in a dimension perpendicular to the longitudinal axis of the elongated distal part and a maximum length l in a dimension parallel to the longitudinal axis. Therein, specifically, the ratio b/l or its reverse value may define the elongation of the shape of the electrode pads. Specifically, the following values may be chosen: $1.5 \le b/l \le 4.0$, specifically $1.8 \le b/l \le 3.0$, more specifically $2.0 \le b/l \le 2.5$, more specifically $b/l=2.21$. For providing the elongated shape, specifically, the electrode pads may have a shape selected from the group consisting of: a rectangular shape; an oval shape; a rectangular shape with rounded edges.

The above-mentioned electrodes of the electrochemical sensor, comprising the working electrode, the reference electrode and the counter electrode, may be arranged on one side or surface of the substrate or may be arranged on two sides or surfaces of the substrate. Specifically, the electrode pads of the working electrode and the reference electrode may be arranged on a first side of the substrate. The counter electrode may be arranged on the same, first side or, more specifically, may be arranged on a second side of the substrate, the second side opposing the first side. The proximal part may comprise at least one working electrode contact pad, at least one reference electrode contact pad and at least one counter electrode contact pad. In case the counter electrode is located on a second side of the substrate, the counter electrode contact pad may be electrically connected to the counter electrode by at least one electrical via extending through the substrate.

The protective measures for the electrode pads may be supported further by arranging the electrode pads of the working electrode in a specific way. Thus, during use of the electrochemical sensor implanted state, the distal part may mainly be bent about an axis perpendicular to the longitudinal extension, wherein a bending radius specifically may be small approximately in a middle portion of the distal part. In order to avoid delamination and/or mechanical stress exerted onto the electrode pads by bending, a specific arrangement of the electrode pads may be chosen. Thus, the elongated distal part may have a length L. The electrode pads of the working electrode may be arranged within an electrode region of the distal part extending over a distance L/3 from a distal end of the substrate towards the proximal part. Consequently, the electrode pads specifically may be arranged closer to the foremost tip of the longitudinal part, specifically in order to reduce mechanical stress.

The electrochemical sensor and the method as proposed herein provide a large number of advantages over known electrochemical sensors and methods of producing the same. Thus, several ways of reducing mechanical and chemical stress may be realized according to this disclosure. Specifically, copper-based electrodes may be realized for which an insulating layer at least partially overlaps on an electrode pad edge. Additionally or alternatively, specifically copper-based electrodes may be realized by using, e.g., rectangular or other elongated shapes for the electrode fields. Owing to the insulating layer overlapping on the electrode pads or the elongated electrode pad design, mechanical stress may be reduced, and delamination becomes less of a risk, specifically in an electrochemical sensor having electrode fields along the distal region of the substrate. Thereby, an electrochemical sensor may be realized, with a working electrode having multiple enzyme fields, wherein the enzyme fields may be disposed, e.g., on copper-gold-based electrode pads that are connected, e.g., via one or a single conductive trace. An insulating layer may at least partially overlap on the electrode pad edge. Additionally or alternatively, the electrode pads may have an elongated shape along the smaller dimension of the substrate.

As outlined above, the corrosive conductive layer specifically may fully or partially be made of copper. The mechanical stability of the adhesion of the copper layer may be enhanced by the above-mentioned protective measure. Specifically, the at least one non-corrosive layer may fully or partially be made of gold. As further outlined above, the substrate specifically may be a flexible substrate, such as a flexible substrate made of, e.g., polyimide. The shape of the pads, specifically the shape of openings in the insulating layer and/or the shape of the electrode pads, specifically may be rectangular, oval or rectangular with rounded edges. The at least one counter electrode specifically may be disposed on a back side, also referred to as a second side, opposing the first side with the at least one working electrode. The counter electrode, specifically the back side counter electrode, specifically may be made of Ag/AgCl. An enzyme paste, specifically an enzyme paste comprising GOD, may be used for filling openings in the insulating layer over electrode pads. Summarizing and without excluding further possible embodiments, the following embodiments may be envisaged:

Embodiment 1: An electrochemical sensor, specifically for detecting an analyte in a body fluid, more specifically an electrochemical sensor for insertion of a body tissue of the user, the electrochemical sensor comprising a substrate having a proximal part and an elongated distal part, wherein a working electrode, a reference electrode and a counter electrode are formed on the distal part, wherein the working electrode comprises a conductive trace along which multiple electrode pads are arranged that are connected via the conductive trace, wherein the electrode pads include a corrosive conductive layer covered by a non-corrosive conductive layer, wherein an insulating layer is disposed on the substrate leaving openings in the area of the electrode pads, wherein the electrochemical sensor comprises at least one protective measure for the corrosive conductive layer selected from the group consisting of:

a. the insulating layer at least partially overlaps on at least one electrode pad edge of at least one of the electrode pads;

b. at least one of the electrode pads has an elongated shape along the smaller dimension of the elongated distal part.

Embodiment 2: The electrochemical sensor according to the preceding embodiment, wherein the corrosive conductive layer is interposed in between the non-corrosive conductive layer and the substrate.

Embodiment 3: The electrochemical sensor according to any one of the preceding embodiments, wherein the non-corrosive conductive layer comprises at least one material more noble than Ag.

Embodiment 4: The electrochemical sensor according to any one of the preceding embodiments, wherein the non-corrosive conductive layer comprises at least one material having a standard potential of more than +0.8 V.

Embodiment 5: The electrochemical sensor according to any one of the preceding embodiments, wherein the corrosive conductive layer comprises at least one material at most as noble as Ag.

Embodiment 6: The electrochemical sensor according to any one of the preceding embodiments, wherein the corrosive conductive layer comprises at least one material having a standard potential of no more than +0.8 V.

Embodiment 7: The electrochemical sensor according to any one of the preceding embodiments, wherein the non-corrosive conductive layer comprises at least one material selected from the group consisting of: Pd; Au; Pt; carbon; graphite; an organic conductor, specifically a conductive polymer; an organic semiconductor, specifically a semiconducting polymer.

Embodiment 8: The electrochemical sensor according to any one of the preceding embodiments, wherein the corrosive conductive layer comprises at least one material selected from the group consisting of: Cu; Ti; Al; Ag.

Embodiment 9: The electrochemical sensor according to any one of the preceding embodiments, wherein the electrode pad comprises at least one corrosive conductive layer—non-corrosive conductive layer pair selected from the group consisting of: Cu—Au; Cu—Pd; Cu—Pt, specifically Cu—Au.

Embodiment 10: The electrochemical sensor according to any one of the preceding embodiments, wherein the insulating layer overlaps the at least one electrode pad edge circumferentially on the full edge of the electrode pad.

Embodiment 11: The electrochemical sensor according to any one of the preceding embodiments, wherein the substrate comprises a polyimide.

Embodiment 12: The electrochemical sensor according to any one of the preceding embodiments, wherein the electrode pads of the working electrode are covered with at least one test chemical, specifically at least one test chemical comprising at least one enzyme for detecting the at least one analyte.

Embodiment 13: The electrochemical sensor according to the preceding embodiment, wherein the insulating layer forms openings on the electrode pads, wherein the openings are fully or partially filled with the at least one test chemical.

Embodiment 14: The electrochemical sensor according to any one of the two preceding embodiments, wherein the test chemical comprises at least one enzyme, carbon particles, a polymer binder and $MnO_2$-particles.

Embodiment 15: The electrochemical sensor according to any one of the three preceding embodiments, wherein the test chemical comprises a layer setup, having at least one test chemical layer comprising at least one enzyme, further having at least one diffusion barrier and at least one biocompatible coating.

Embodiment 16: The electrochemical sensor according to any one of the preceding embodiments, wherein the insulating layer comprises at least one solder resist.

Embodiment 17: The electrochemical sensor according to any one of the preceding embodiments, wherein the electrode pads have an elongated shape having a maximum width w in a dimension perpendicular to a longitudinal axis of the elongated distal part and a maximum length l in a dimension parallel to the longitudinal axis, wherein $1.5 \leq b/l \leq 4.0$, specifically $1.8 \leq b/l \leq 3.0$, more specifically $2.0 \leq b/l \leq 2.5$, more specifically $b/l=2.21$.

Embodiment 18: The electrochemical sensor according to any one of the preceding embodiments, wherein the electrode pads have a shape selected from the group consisting of: a rectangular shape; an oval shape; a rectangular shape with rounded edges.

Embodiment 19: The electrochemical sensor according to any one of the preceding embodiments, wherein the electrode pads of the working electrode and the reference electrode are arranged on a first side of the substrate.

Embodiment 20: The electrochemical sensor according to the preceding embodiment, wherein the counter electrode is arranged on a second side of the substrate, the second side opposing the first side.

Embodiment 21: The electrochemical sensor according to the preceding embodiment, wherein the proximal part comprises at least one working electrode contact pad, at least one reference electrode contact pad and at least one counter electrode contact pad, wherein the counter electrode contact pad is electrically connected to the counter electrode by at least one electrical via extending through the substrate.

Embodiment 22: The electrochemical sensor according to any one of the preceding embodiments, wherein the counter electrode comprises Ag/AgCl.

Embodiment 23: The electrochemical sensor according to any one of the preceding embodiments, wherein the elongated distal part has a length L, wherein the electrode pads of the working electrode are arranged within an electrode region of the distal part extending over a distance L/3 from a distal end of the substrate towards the proximal part.

Embodiment 24: A method for producing an electrochemical sensor, the method comprising:

a) providing a substrate having a proximal part and an elongated distal part;

b) forming a working electrode, a reference electrode and a counter electrode on the distal part, wherein the working electrode comprises a conductive trace along which multiple electrode pads are arranged that are connected via the conductive trace, wherein the electrode pads include a corrosive conductive layer covered by a non-corrosive conductive layer; and c) disposing an insulating layer on the substrate leaving openings in the area of the electrode pads;

wherein the method further comprises:

d) providing at least one protective measure for the corrosive conductive layer selected from the group consisting of:

d1. the insulating layer at least partially overlaps on at least one electrode pad edge of at least one of the electrode pads;

d2. at least one of the electrode pads has an elongated shape along the smaller dimension of the elongated distal part.

Embodiment 25: The method according to the preceding embodiment, wherein the method comprises manufacturing the electrochemical sensor according to any one of the preceding embodiments referring to an electrochemical sensor.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIGS. 8A, 8B and 8C show various test setups of an electrode field;

FIG. 9 shows oxidation currents for various test setups under mechanical stress.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
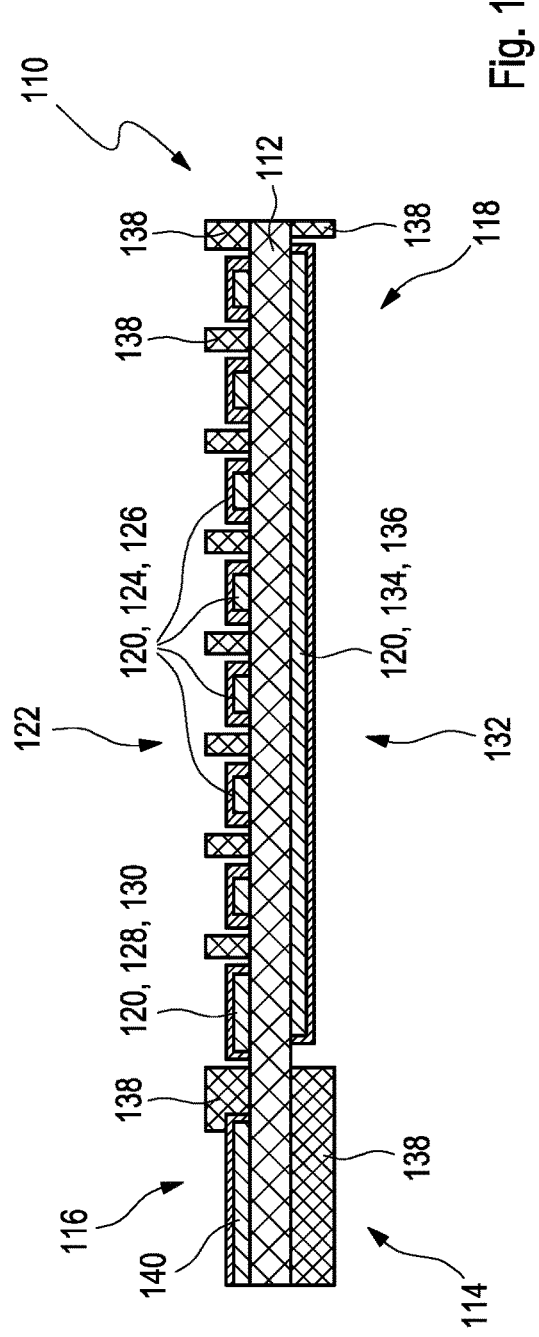
FIG. 1 shows a cross-sectional view of a transcutaneously insertable electrochemical sensor for detecting an analyte in a body fluid.

In FIG. 1, a cross-sectional view along a longitudinal axis of an electrochemical sensor 110 for detecting an analyte in a body fluid is shown. The electrochemical sensor 110 specifically may be suited for insertion into a body tissue of a user. In the electrochemical sensor 110 according to FIG. 1, protective measures as presently proposed and as explained in further detail below may be implemented.

The electrochemical sensor 110 comprises a substrate 112, the substrate having a proximal part 114 with a contact portion 116, and a distal part 118, which, as will be outlined in further detail below, has an elongated shape.

The electrochemical sensor 110 has a plurality of electrode fields 120. Thus, on a first side 122 of the substrate 112, which may also be referred to as an upper side or front side, a working electrode 124 is disposed, having a plurality of interconnected working electrode fields 126 as well as a reference electrode 128 having a reference electrode field 130. On a second side 132, which may also be referred to as a back side or bottom side, a counter electrode 134 is disposed, having a counter electrode field 136. The counter electrode 134 and the reference electrode 128 both may comprise Ag/AgCl. The electrode fields 120 may be separated by at least one insulating layer 138, such as a solder resist, which partially covers the substrate 112. The substrate 112 itself may be a flexible substrate, such as a polyimide substrate.

The electrochemical sensor 110 may further comprise electrical contact pads 140 for electrically contacting the electrode fields 120, e.g., via conductive traces, which will be explained in further detail below, e.g., with respect to FIGS. 6 and 7 below, and which are not visible in FIG. 1.

Figure 2:
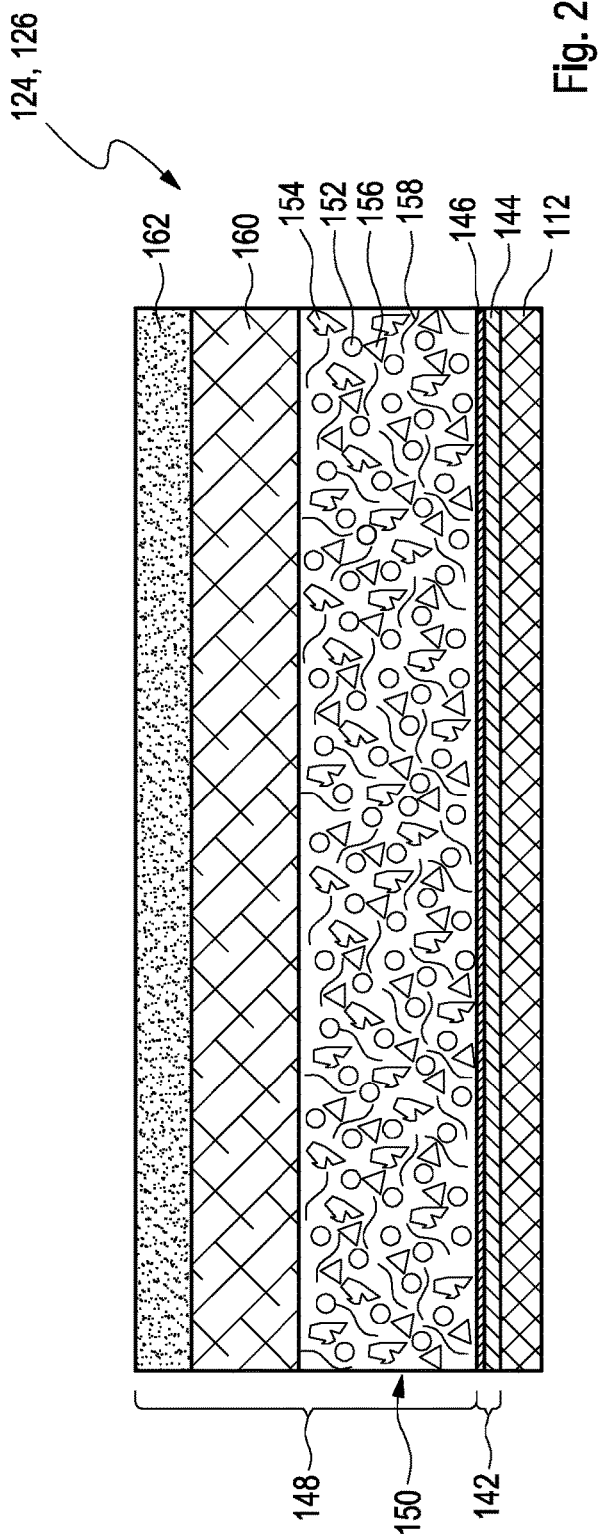
FIG. 2 shows a cross-sectional view through an electrode field of the working electrode of the electrochemical sensor of FIG. 1.

In FIG. 2, a cross-sectional view through a layer setup of a working electrode field 126 of the working electrode 124 is shown. In this exemplary embodiment, the polyimide substrate 112, as an example, carries an electrode pad 142. The electrode pad 142 itself comprises a corrosive conductive layer 144 which, as an example, may be made of copper (Cu). On top of the corrosive conductive layer, at least one non-corrosive conductive layer 146 is disposed, such as a gold layer.

On top of the electrode pad 142, at least one test chemical 148 is disposed. In the exemplary embodiment shown in FIG. 2, as an example, the at least one test chemical 148 may comprise at least one enzyme layer 150. The at least one enzyme layer 150, as an example, may comprise at least one enzyme 152, such as glucose dehydrogenase (GOD). Further, the enzyme layer 150 may comprise carbon particles 154, which are electrically conductive. The enzyme layer 150 may further comprise $MnO_2$ particles 156 as well as a polymer binder 158.

On top of the enzyme layer 150, a diffusion barrier 160 may be disposed, which may prevent a diffusion of materials from the enzyme layer 150 into the body tissue and/or into a body fluid, whereas an analyte may enter the enzyme layer 150 from the body tissue and/or from the body fluid. The diffusion barrier, as an example, may have a thickness of 15 to 18 μm and, as an example, may be made of a hydrophilic polymer, such as a thermoplastic polyurethane. On top of the diffusion barrier 160, one or more layers of biocompatibility coating 162 may be disposed, such as one or more layers of a hydrogel. As an example, the biocompatibility coating 162 may have a thickness of 4 to 6 μm.

Figure 3:
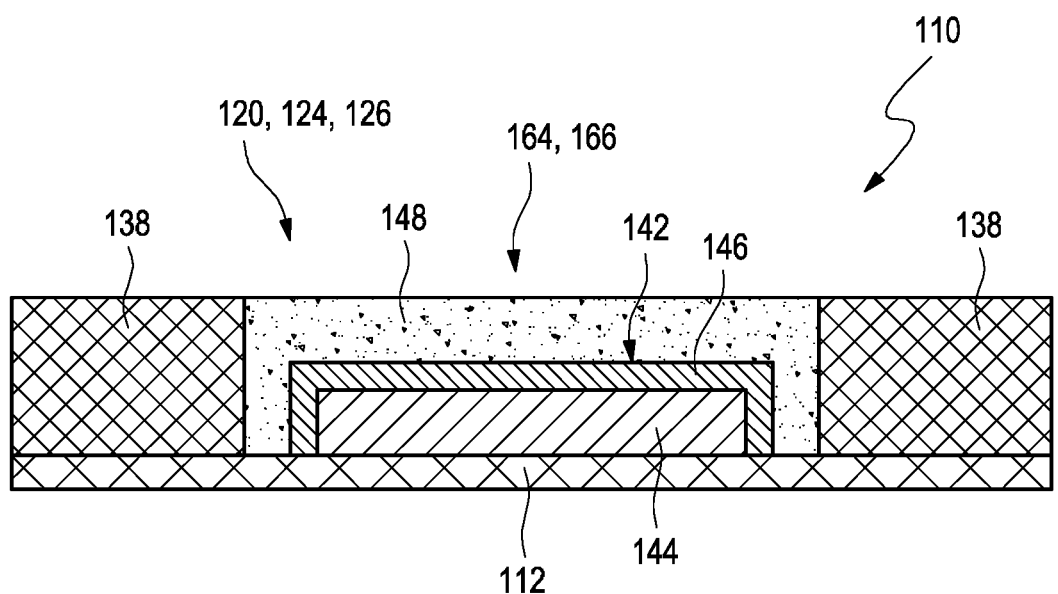
FIG. 3 shows a cross-sectional view as in FIG. 2, with non-overlapping insulating layer.

In FIG. 3, a working electrode field 126 of a working electrode 124 is shown in further detail and in a larger field of view, not to scale. The setup basically corresponds to the layer setup shown in FIG. 2, with the substrate 112, and the insulating layer 138 on top of the substrate 112, with openings 164 in the insulating layer 138, forming a window 166 for each working electrode field 126. As discussed above in the context of FIG. 2, within the window 166, the electrode pad 142 is disposed, with the corrosive conductive layer 144 and the non-corrosive conductive layer 146 on top, such as the copper layer with the gold layer on top. On top of the electrode pad 142, the test chemical 148 is disposed.

For manufacturing the setup of FIG. 3, as an example, the polyimide substrate 112 may be coated, in a large-area coating such as a lamination process, with copper. During manufacturing, the copper layer may then be patterned. Onto the patterned copper layer, the gold layer may be deposited, such as by using galvanic coating. In between the copper and the polyimide, a material-bonded connection may exist, as is the case in between the gold layer and the copper layer through the galvanic deposition. In between the gold layer and the polyimide, typically, no connection is established.

Figure 4:
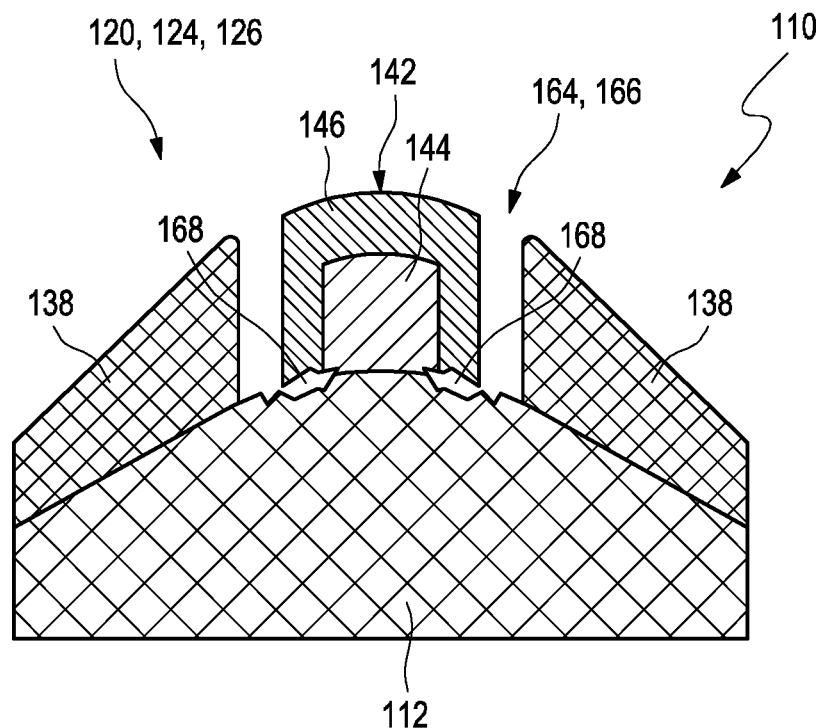
FIG. 4 shows the setup of FIG. 3 and the problem of delamination under mechanical stress.

In FIG. 4, a technical challenge is shown which arises from mechanical stress when the substrate 112 in the setup of FIG. 3 is bent. The test chemical 148 is not shown in this schematic view.

As can be seen in FIG. 4, when the electrochemical sensor 110 is bent, different types of mechanical stress typically are induced into the layers. Thus, stress by pulling and/or stress by pressure may be exerted, which both may lead to a delamination of the gold from the polyimide. As indicated by reference number 168 in FIG. 4, regions with an exposed corrosive conductive layer 144 may occur due to this exertion of stress. In these regions, the corrosive conductive material, such as copper, is electrochemically exposed and, locally, is no longer protected by the non-corrosive conductive material such as gold. When operating the electrochemical sensor, thereby, the corrosive conductive material is oxidized and leads to an error current. Thus, the electrochemical sensor 110, when exerting mechanical stress such as by bending the substrate 112, may both be mechanically destroyed and may provide faulty measurements, which are falsified by oxidation currents.

Figure 5:
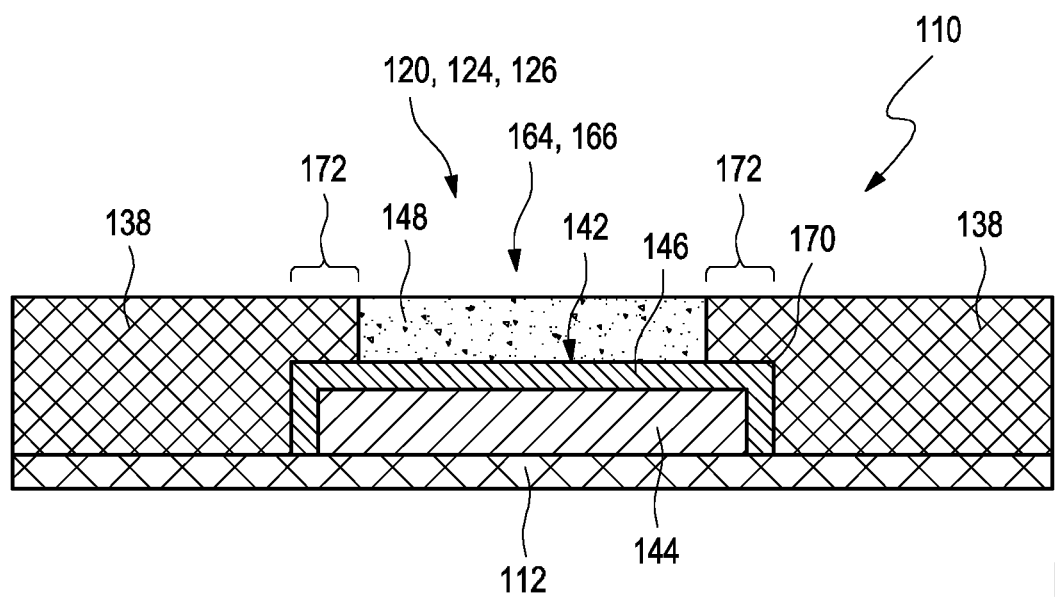
FIG. 5 shows the setup of FIG. 3 with overlapping insulating layer.

In FIG. 5, as a first option for providing a protective measure against the effects shown in FIG. 4, the setup of FIG. 3 is shown, with the modification of the insulating layer 138 overlapping an electrode pad edge 170 of the working electrode pad 142. Thus, in an overlap region 172, preferably on all sides of the electrode pad 142, the insulating layer 138 overlaps with the electrode pad 142 and, thus, protects the electrode pad edge 170 from delamination and/or exposure to electrochemical reactions, even under stress. Thus, the solder resist may be pulled over the edge 170 of the working electrode pad 142.

In order to maintain the size of the printed working electrode 124 and, specifically, of the single working electrode fields 126, the size of the opening 164 may be maintained as compared to the conventional setup in FIG. 3 and, consequently, the size of the electrode pad 142 may be increased, such that the edge 170 is covered by the insulating layer 138. Even if, when bending the substrate 112, regions with exposed corrosive conductive layer 168 should occur, these regions 168 still are covered by the insulating layer 138 and, thus, sealed against electrochemical reactions.

Figure 6:
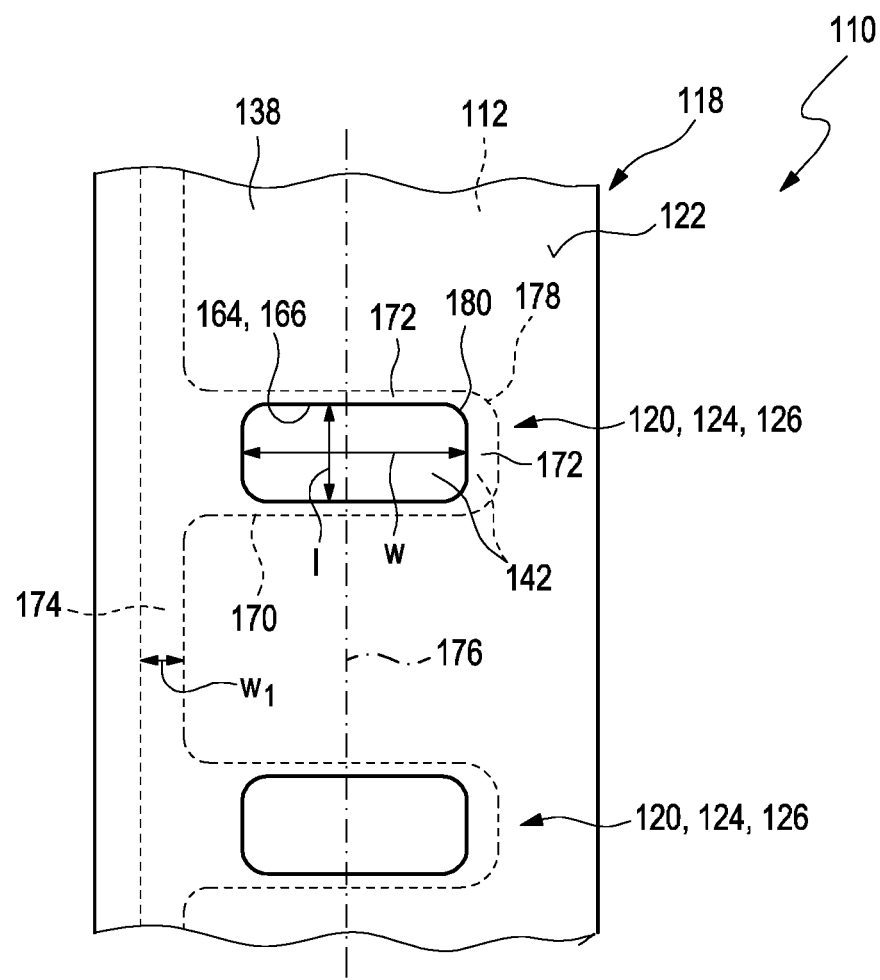
FIG. 6 shows a top view onto working electrode fields having an elongated shape, with overlapping insulating layer.

In FIG. 6, a top view onto a part of the first side 122 of the distal part 118 of the electrochemical sensor 110 is shown. In this top view, for the first time, a conductive trace 174 is also visible, which interconnects the working electrode fields 126 of the working electrode 124. The conductive trace 174, as an example, may have a width $w_1$, perpendicular to a longitudinal axis of extension 176 of the elongated distal part 118 of the substrate 112, which, as an example, may be approximately 0.05 mm. The electrode pads 142, as visible herein, may, at their edges 170, be covered by the insulating layer 138, as in FIG. 5.

The setup of FIG. 6 further shows a second option for providing a protective measure for the corrosive conductive layer, which is the option of providing the electrode pads 142 as having an elongated shape along the smaller dimension of the elongated distal part 118. Thus, as can be seen in FIG. 5, the working electrode pads 142 have a width w in a dimension perpendicular to the longitudinal axis 176 of the elongated distal part 118 which exceeds a length l in a direction parallel to the longitudinal axis 176. As an example, the ratio w/l may be in the range of 2.1 to 2.2, such as by providing w in the setup of FIG. 6 as 0.31 mm and by providing the length l in the range of 0.15 mm. It shall be noted, however, that other dimensions are feasible, even though the values shown herein are generally well suitable. For ranges of w/l, reference may be made to the description given above.

As further shown herein, the corners 178 of the electrode pads 142, as well as the corners 180 of the windows 166 may be rounded. As an example, the corners 178 may have a radius of curvature of 53 µm for gold, and 50 µm for copper. Other extensions are possible. The overlap regions 172, as an example, may have a width of 45 µm. Other dimensions are feasible.

Figure 7:
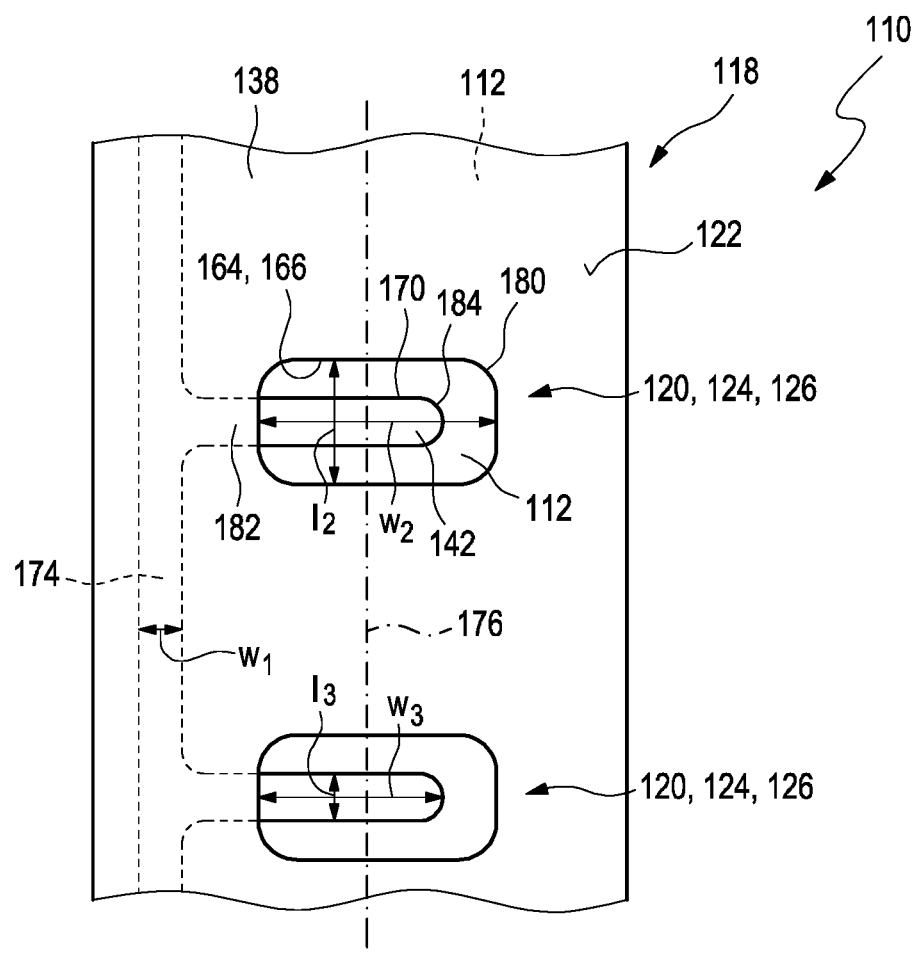
FIG. 7 shows the setup of FIG. 6 with non-overlapping insulating layer.

In FIG. 7, an alternative embodiment is shown, with no overlapping regions 172. The setup, firstly, widely corresponds to the embodiment shown in FIG. 6, so reference may be made to the description of this figure for many details. Again, a conductive trace 174 is provided for interconnecting the electrode pads 142 of the working electrode fields 126 of the working electrode 124. Further, again, openings 164 are provided within the insulating layer 138 which partially covers the substrate 112, forming windows 166 with, optionally, rounded corners 180. Further, again, working electrode contact pads 142 are provided having an elongated shape with a longer axis perpendicular to the longitudinal axis 176 of the elongated distal part 118 of the substrate 112. As shown therein, however, the edges 170 of the electrode pads 142, in this embodiment, are not covered by the insulating layer 138, such that, within the windows 166 and in between the insulating layer 138 and the edges 170, the substrate 112 is uncovered and visible. In this embodiment, the working electrode pad 142 may be defined as the portion of the conductive layers 144, 146 visible within the window 166, whereas a portion in between the window 166 and the conductive trace 174 may be defined as an interconnecting portion 182. As an example, the electrode pad 142 may have a width $w_3$ and a length $l_3$, with $w_3$=200 µm and l3=50 µm. The window 166, contrarily, may have a width $w_2$ of 310 µm, and a length $l_2$ of 150 µm. The electrode pads 142, at a side facing away from the conductive trace 174, may have a curvature 184, with a radius of curvature of, e.g., 22 µm for copper and 25 µm for gold.

The various options for providing a protective measure for the electrode pads 142 and, specifically, for the corrosive conductive layer 144 were evaluated by FEM simulations. For this purpose, three different setups of working electrodes were simulated, which are shown in FIGS. 8A to 8C. Therein, a distal end 186 of an electrochemical sensor 110 is shown in each case, with three different setups for a working electrode field 126 of a working electrode 124: In FIG. 8A, a conventional setup is shown, with a round working electrode field 126, with the insulating layer 138 forming an opening 164 and window 166 having a round shape, with the electrode pad 142 being smaller than the window 166. In FIG. 8B, the situation of the setup of FIG. 7 is shown, with an elongated window 166 and an elongated electrode pad 142, in a direction perpendicular to the longitudinal axis 176. In FIG. 8C, the situation of FIG. 6 is shown, with an elongated electrode pad 142 and window 166 and with the insulating layer 138 overlapping the edges 170 of the electrode pad 142.

Electrochemical sensors of the types shown in FIGS. 8A to 8C were bent about an axis perpendicular to the longitudinal axis 176, with the proximal part 114 fixed and the distal part 118 bent upwardly. The setup of FIG. 8A was considered as the status quo, having a contact tension between the gold layer and the polyimide substrate of 1. The setup of FIG. 8B turned out to have a reduced contact tension between Au and the polyimide substrate of −61%, the setup of FIG. 8C turned out to have a reduced contact tension of −58%.

In FIG. 9, various measurements for oxidation currents I, given in nanoamperes, are shown as a function of the bending angle α. Therein, the electrical current curves 188 are curves measured for the conventional setup of the electrodes as shown in FIG. 8A, with a symmetric electrode design and with non-overlapping insulating layer 138. Curves 190 are measured oxidations currents for the setup of FIG. 8B, i.e., an electrode setup with an elongated shape in a direction perpendicular to the longitudinal axis 176, but with non-overlapping insulating layer 138. Curves 192 demonstrate measured currents for the setup of FIG. 8C, with an electrode design having an elongated shape in a direction perpendicular to the longitudinal axis 176 and, further, with an overlapping insulating layer 138. Finally, for comparison, curves 194 are curves measured for the setup shown in FIG. 5, with a symmetric design as in FIG. 8A, but with overlapping electrically insulating layer 138. As is visible, e.g., when comparing curves 188 with one or more of curves 190, 192, 194, all of the protective measures, both taken in isolation or taken in combination, lead to a reduced oxidation current when bending the substrate 112. Thus, the electrode pads are protected both mechanically and electrochemically. In curves 190 and 192, when bending the substrate, the oxidation current of the copper layer of the electrochemical sensors rises significantly later as compared to curves 188. Curves 192 and 194, both for variants with an overlap between the insulating layer and the electrode pad, do not differ significantly and, both, rise significantly later, i.e., at larger bending angles, as compared to curves 190, representing a variant without overlap.

Figure 10:
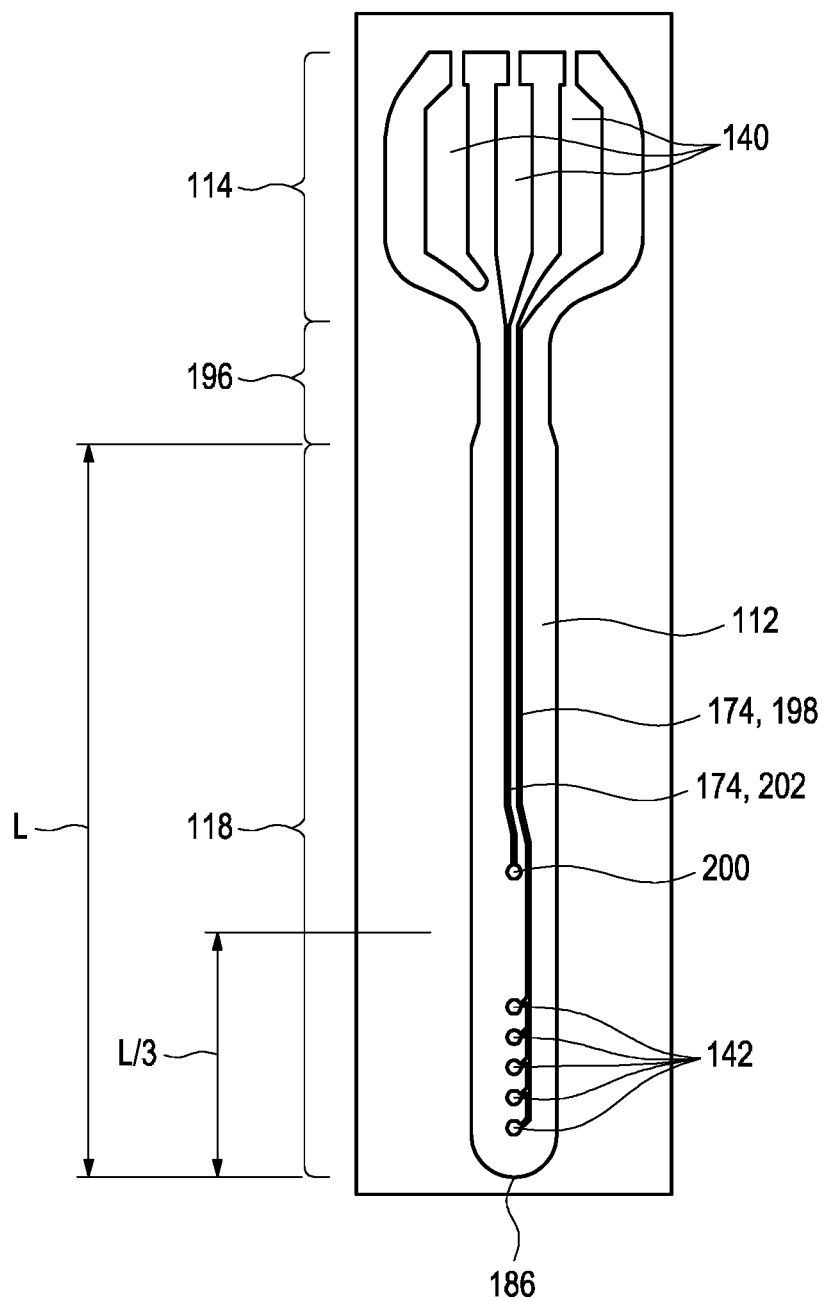
FIG. 10 shows a top view of an electrochemical sensor configuration having working electrode fields located in the foremost distal end of the sensor substrate.

The curves in FIG. 9 were all measured with electrochemical sensors having eight working electrode fields 126, each electrode field 126 having an electrode pad 142. When bending the electrochemical sensor 110 by 45°, the FEM simulations indicate that the first three of these eight electrodes, counted from the reference electrode 128, are subject to larger mechanical stress as compared to the remaining electrode fields 120. Thus, in addition to the above-mentioned protective measures, further design measures may be taken in order to reduce mechanical and electrochemical stress onto the electrode pads 142 of the working electrode 124. Thus, in FIG. 10, an embodiment of a substrate 112 for an electrochemical sensor 110 is shown, which may be combined with the above-mentioned measures of designing appropriate working electrode fields 126. In this embodiment, again, the substrate 112 comprises a proximal part 114 and an elongated distal part 118, for transcutaneous insertion into a body tissue of a user. In between the distal part 118 and the proximal part 114, as shown in FIG. 10, a narrowed intermediate part 196 may be present. Further shown in FIG. 10 are contact pads 140, with the right contact pad 140 in this figure being connected to working electrode pads 142 via a working electrode conductive trace 198. The middle one of the contact pads 140 may be connected to a reference electrode pad 200 via at least one reference electrode conductive trace 202. The remaining one of the contact pads 140 may be connected to a corresponding counter electrode contact pad on a reverse side of the substrate 112 via an electrical via, which is not shown in FIG. 10.

The electrode pads 142, in this simplified figure, may be designed according to any one of the embodiments shown above, e.g., according to FIG. 6 or FIG. 7. Thus, an elongated shape may be provided. Further, the insulating layer 138 is not shown in this setup. Thus, overlap just as discussed above may be provided, as a further protective measure.

As shown in FIG. 10, the number of working electrode pads 142 is reduced, from originally eight to five. Further, since mechanical stress typically is largest in the middle of the elongated distal part 118, the electrode pads 142 are located close to a distal end 186 of the elongated distal part 118. Thus, as an example, the elongated distal part 118, in total, may have a length L, from the distal end 186 to the beginning of the narrowed intermediate part 196. The electrode pads 142 of the working electrode 124 may all be arranged within a distance L/3 from the distal end 186. Thereby, when bending the substrate 112, the mechanical stress onto the sensitive working electrode pads 142 may further be reduced.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 electrochemical sensor
112 Substrate
114 proximal part
116 contact portion
118 distal part
120 electrode fields
122 first side
124 working electrode
126 working electrode field
128 reference electrode
130 reference electrode field
132 second side
134 counter electrode
136 counter electrode field
138 insulating layer
140 contact pads
142 electrode pad
144 corrosive conductive layer
146 non-corrosive conductive layer
148 test chemical
150 enzyme layer 152 Enzyme
154 carbon particles
156 $MnO_2$ particles
158 polymer binder
160 diffusion barrier
162 biocompatibility coating
164 Opening
166 Window
168 regions with exposed corrosive conductive layer
170 electrode pad edge
172 overlap region
174 conductive trace
176 longitudinal axis
178 Corner
180 Corner
182 interconnecting portion
184 Curvature
186 distal end
188 curves for setup of FIG. 8A
190 curves for setup of FIG. 8B
192 curves for setup of FIG. 8C
194 curves for setup of FIG. 5
196 intermediate part
198 working electrode conductive trace
200 reference electrode pad
202 reference electrode conductive trace

What is claimed is:

1. An electrochemical sensor, comprising:
a substrate having a proximal part and an elongated distal part;
a working electrode, a reference electrode and a counter electrode formed on the distal part;
the working electrode forming a conductive trace;
multiple electrode pads arranged along and connected by the conductive trace, wherein the electrode pads include a corrosive conductive layer covered by a non-corrosive conductive layer, wherein the corrosive conductive layer comprises at least one metal being less noble or as noble as Ag, and the non-corrosive conductive layer comprises at least one metal being more noble than Ag;
an insulating layer disposed on the substrate and forming openings in the areas of the electrode pads; and
a protective measure for the corrosive conductive layer selected from the group consisting of (a) the insulating layer at least partially overlaps at least one electrode pad edge of at least one of the electrode pads and (b) at least one of the electrode pads has an elongated shape along the smaller dimension of the elongated distal part.

2. The electrochemical sensor according to claim 1, wherein the corrosive conductive layer is interposed between the non-corrosive conductive layer and the substrate.

3. The electrochemical sensor according to claim 1, wherein the non-corrosive conductive layer comprises at least one material selected from the group consisting of Pd, Au, Pt, carbon, graphite, an organic conductor, an organic semiconductor.

4. The electrochemical sensor according to claim 1, wherein the corrosive conductive layer comprises at least one material selected from the group consisting of Cu, Ti, Al, Ag.

5. The electrochemical sensor according to claim 1, wherein the electrode pad comprises a conductive layer pair selected from the group consisting of Cu—Au, Cu—Pd, Cu—Pt.

6. The electrochemical sensor according to claim 1, wherein the insulating layer overlaps at least one edge of one of the electrode pads circumferentially on the entire said edge of the one electrode pad.

7. The electrochemical sensor according to claim 1, wherein the substrate comprises a polyimide.

8. The electrochemical sensor according to claim 1, wherein the electrode pads are covered with a test chemical.

9. The electrochemical sensor according to claim 8, wherein the test chemical comprises at least one enzyme for detecting at least one analyte.

10. The electrochemical sensor according to claim 8, wherein the test chemical comprises an enzyme, carbon particles, a polymer binder, and $MnO_2$-particles.

11. The electrochemical sensor according to claim 1, wherein the insulating layer comprises at least one solder resist.

12. The electrochemical sensor according to claim 1, wherein the electrode pads have an elongated shape having a width (w) in a dimension perpendicular to a longitudinal axis of the elongated distal part and a length (l) in a dimension parallel to the longitudinal axis, wherein the ratio of width to length is $1.5 \leq w/l \leq 4.0$.

13. The electrochemical sensor according to claim 1, wherein the electrode pads have a shape selected from the group consisting of a rectangular shape, an oval shape, and a rectangular shape with rounded edges.

14. The electrochemical sensor according to claim 1, wherein the elongated distal part has a length L, wherein the electrode pads of the working electrode are arranged within an electrode region of the distal part extending over a distance L/3 from a distal end of the substrate towards the proximal part.

15. The electrochemical sensor according to claim 1, wherein the non-corrosive conductive layer has a larger area than the corrosive conductive layer.

16. The electrochemical sensor according to claim 15, wherein edges of the non-corrosive conductive layer are bonded directly to the substrate.

17. The electrochemical sensor according to claim 1, wherein the non-corrosive layer overlaps at least the edges of the corrosive layer and the insulator overlaps at least the edges of the non-corrosive layer.

18. A method for producing an electrochemical sensor, comprising the following steps:
a) providing a substrate having a proximal part and an elongated distal part;
b) forming a working electrode, a reference electrode and a counter electrode on the distal part, the forming of the working electrode including forming a conductive trace along which multiple electrode pads are arranged and connected via the conductive trace, wherein forming the electrode pads includes providing a corrosive conductive layer covered by a non-corrosive conductive layer; and
c) disposing an insulating layer on the substrate and leaving openings in the insulating layer in the area of the electrode pads; and
d) providing at least one protective measure for the corrosive conductive layer selected from the group consisting of (d1) having the insulating layer at least partially overlap on at least one electrode pad edge of at least one of the electrode pads and (d2) providing at least one of the electrode pads with an elongated shape along the smaller dimension of the elongated distal part.

* * * * *